United States Patent [19]

Hopp

[11] Patent Number: 4,627,122
[45] Date of Patent: Dec. 9, 1986

[54] HOSPITAL BED, METHOD OF MAKING SAME AND COMPONENTS THEREFOR

[75] Inventor: Marcel F. Hopp, Cincinnati, Ohio

[73] Assignee: Standard Textile Co. Inc., Cincinnati, Ohio

[21] Appl. No.: 581,576

[22] Filed: Feb. 21, 1984

[51] Int. Cl.⁴ .............................................. A47G 9/00
[52] U.S. Cl. ............................................. 5/484; 5/487
[58] Field of Search ............................. 5/482, 484, 487

[56] References Cited

U.S. PATENT DOCUMENTS

| 2,414,927 | 1/1947 | Chapman | 5/484 |
| 2,779,035 | 1/1957 | McMurry | 5/484 |
| 3,286,284 | 11/1966 | Klogether et al. | 5/484 |
| 3,646,624 | 3/1972 | Zipf, III | 5/484 |
| 4,064,577 | 12/1977 | Walters | 5/484 |
| 4,391,010 | 7/1983 | Kronman | 5/484 |

FOREIGN PATENT DOCUMENTS

| 481762 | 3/1952 | Canada | 5/484 |
| 2119708 | 11/1983 | United Kingdom | 5/484 |

Primary Examiner—Gary L. Smith
Assistant Examiner—Michael F. Trettel
Attorney, Agent, or Firm—Kinney & Schenk

[57] ABSTRACT

A bed for a hospital or the like, method of making same, and components therefor are provided wherein such bed comprises a mattress assembly, a bottom sheet covering the mattress assembly, a waterproof layer covering the central portion of the bottom sheet, and a cover over such layer wherein the layer has tails extending from its opposite ends and cover comprises a water-absorbent pad which also has tails extending from its opposite ends; and the tails are adapted to be disposed under the mattress assembly to hold the layer and pad securely on the bottom sheet with the layer and pad being readily removable from the bed for laundering thereof by pulling the tails from under the mattress assembly.

20 Claims, 4 Drawing Figures

U.S. Patent  Dec. 9, 1986  4,627,122
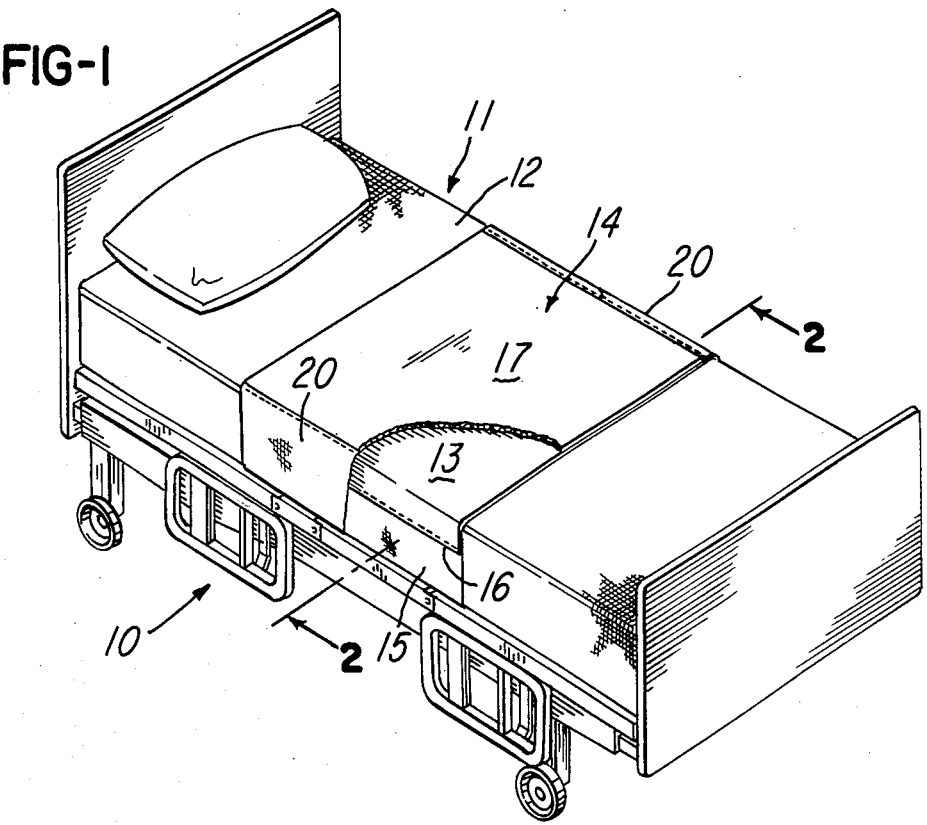
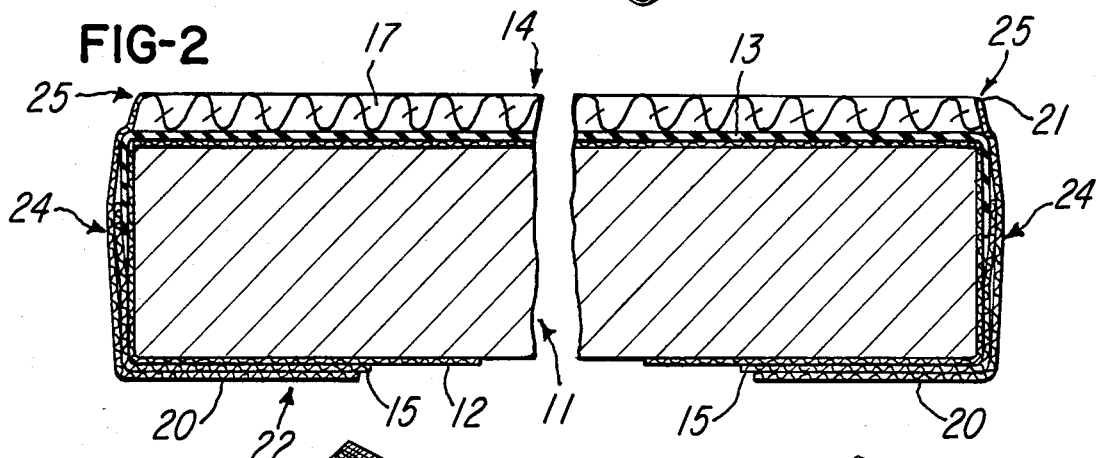
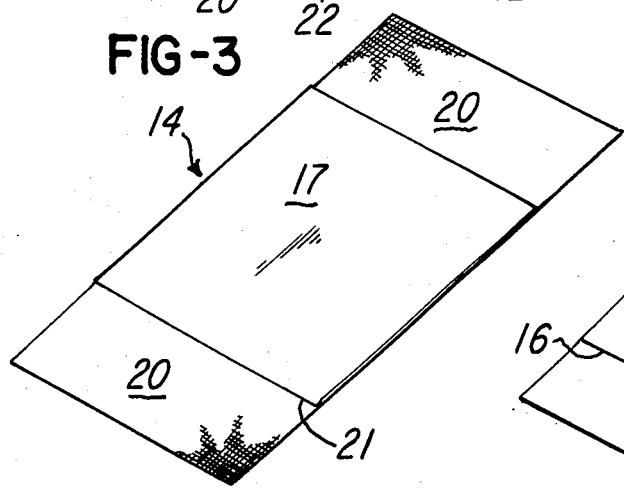
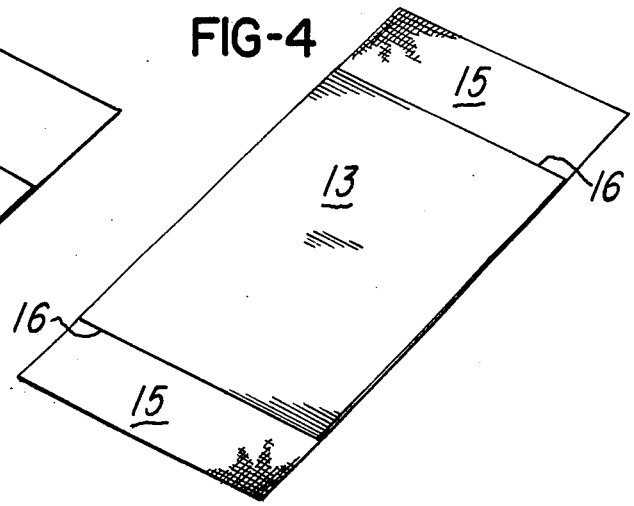

4,627,122

HOSPITAL BED, METHOD OF MAKING SAME AND COMPONENTS THEREFOR

BACKGROUND OF THE INVENTION

1. Field of the Invention

This invention relates to a bed for a hospital or the like, to a method of making such bed, and to components for such bed.

2. Prior Art Statement

Patients suffering from incontinence and confined to a bed in a hospital, nursing home, and similar health care facility present special problems to health care professionals in their efforts to keep such patients comfortable by maintaining their general bed linens such as sheets, mattresses, mattress pads, and the like in a clean and sanitary condition. It is especially difficult with these patents to keep moisture away from their bodies. Although, it is possible to repeatedly change the usual bed linens, mattress pads, and the like, this is an expensive and time consuming proposition and still does not always assure that the patient is in an optimum sanitary and moisture-free situation.

It is known in the art to provide a bed for a hospital or the like which comprises mattress means, a bottom sheet covering the mattress means, a waterproof layer covering the central portion of the bottom sheet, and a cover over the layer.

However, each waterproof layer of the type previously proposed for use over the central portion of mattress means of a hospital bed or the like is generally comparatively easily dislodged. Similarly, the cover over such a waterproof layer has generally been in the form of a draw sheet or the like and the water absorbing capability of such a cover has been quite poor, resulting in the patient having to be in contact with moisture of a soiled draw sheet or cover and thereby causing considerable discomfort.

Accordingly, it is quite clear that previously proposed beds for hospitals or the like have deficiencies.

SUMMARY OF THE INVENTION

This invention provides an improved bed for a hospital or the like comprising mattress means, a bottom sheet covering the mattress means, a waterproof layer covering the central portion of the bottom sheet, and a cover over the layer.

In accordance with one embodiment of this invention the improved bed has the layer thereof provided with tails extending from its opposite ends and the cover comprises a water-absorbent pad which also has tails extending from its opposite ends. The tails are adapted to be disposed under the mattress means to hold the layer and pad securely on the bottom sheet and the layer and pad are readily removable from the bed for laundering thereof by pulling the tails from under the mattress means.

Accordingly, it is an object of this invention to provide an improved bed of the character mentioned for a hospital, nursing home, health care facility, or the like.

Another object of this invention is to provide an improved method making a bed of the character mentioned.

Another object of this invention is to provide an improved waterproof layer for a bed of the character mentioned wherein such layer comprises tails extending from its opposite ends.

Another object of this invention is to provide an improved cover for use on a bed of the character mentioned wherein such cover comprises an improved moisture-absorbent pad and tails extending from its opposite ends.

Other features, objects, uses, and advantages of this invention are apparent from a reading of this description which proceeds with reference to the accompanying drawing forming a part thereof.

BRIEF DESCRIPTION OF THE DRAWING

The accompanying drawing shows present preferred embodiments of this invention, in which FIG. 1 is an isometric view, with parts broken away, illustrating an exemplary bed for a hospital or the like and made in accordance with the teachings of this invention;

FIG. 2 is an enlarged cross-sectional view with the central portion thereof broken away taken essentially on the line 2—2 of FIG. 1;

FIG. 3 is an isometric view illustrating an exemplary cover adapted to be used on the bed of FIG. 1; and FIG. 4 is an isometric view illustrating a waterproof layer adapted to be used on the bed of FIG. 1.

DETAILED DESCRIPTION

Reference is now made to FIG. 1 of the drawing which illustrates one exemplary embodiment of a bed of this invention which is designated generally by the reference numeral 10. The bed 10 is particularly adapted for use in a hospital, nursing home, health care facility, or the like and such bed comprises mattress means which is designated generally by the reference numeral 11 in FIGS. 1 and 2 and a bottom sheet 12 covering the mattress means. The mattress means may be any suitable mattress or mattress assembly which may include integral spring means or separate box springs and in each instance a mattress pad is provided thereover and as is known in the art. The bed 10 also comprises a waterproof layer 13 covering the central portion of the bottom sheet 12 and hence the central portion of the mattress means 11 and a cover 14 is disposed over the waterproof layer 13.

In accordance with the teachings of this invention and as shown in FIGS. 2 and 4, the layer 13 has tails, each designated by the reference numeral 15, extending from its opposite ends 16 and the layer 13 will be described in more detail subsequently. As shown in FIGS. 2 and 3, the cover 14 comprises a water-absorbent pad 17 which also has tails, each designated by the reference numeral 20, extending from its opposite ends 21.

The tails 15 and 20 are adapted to be disposed under the mattress means, as shown typically at 22 in FIG. 2, for example, to hold the layer 13 and pad 17 securely on the bottom sheet 12. In actual use the tails are sandwiched under parts of the mattress means and supporting structure (not shown in FIG. 2) for such mattress means. The layer and pad are readily removed from the bed 10 for laundering thereof simply by pulling the tails 15 and 20 from under the mattress means 11.

The waterproof layer 13 is preferably made of a sheet of moisture impervious polymeric material such as a suitable plastic material, rubber, or the like. The preferred material is neoprene rubber. The layer 13 also has tails 15 as previously mentioned and the tails of layer 13 are preferably made of a fabric material. The tails 15 may be attached to the waterproof layer 13 using any suitable means known in the art and may be adhesively fastened, sewn or the like. Preferably the tails 15 are sewn in place employing conventional stitches as are known in the art.

It will also be appreciated that the fabric material defining the tails 15 may be a suitable rectangular strip or web of scrim material having a particular width and a length such that the opposite end portions of the length define the tails. The polymeric layer in the form of neoprene may be suitably bonded or otherwise coated in an adhering manner against the central portion of the scrim material. The scrim material may be a natural or a synthetic fabric and preferably is in the form of a flame resistant synthetic fabric consisting of nylon, or the like.

The cover 14 comprising the bed 10 has a pad 17 as previously mentioned and tails 20 extending from opposite ends of the pad 17. The pad 17 is comprised of warps and wefts and preferably is a plainwoven or squarewoven fabric. The threads defining either the warps or the wefts may consist of natural threads and synthetic threads. The preferred combination of threads is 50% natural threads in the form of cotton and 50% synthetic threads in the form of polyester.

The pad of the cover 14 is also comparatively thick when compared with an ordinary sheet used on a hospital bed and such pad is capable of absorbing water in an optimum manner. In particular, the pad is of such a weight that the threads defining such pad have a weight of approximately 18 ounces per square yard. It will also be appreciated that in the usual cover 14, the tails 20 thereof are also preferably sewn in position utilizing any suitable stich known in the art. The tails 20 may also be made of a suitable fabric material which may be standard sheeting material, or the like.

The cover 14 is dimensioned such that prior to washing thereof it is about the same size as the waterproof layer 13. However, the construction of the pad 15 is such that it shrinks substantially, the entire amount that it is going to shrink once it has been suitably laundered the first few times. After laundering it is such that it is comparatively smaller in size in the dimension transverse the length of the bed for a purpose to be subsequently described. Similarly the dimension of the pad 17 in the direction of the length of the bed is roughly equal, generally smaller, than the corresponding dimension of the waterproof layer 13 so that no portion of pad 17 is in contact with the bottom sheet 12. In this manner moisture in pad 17 is isolated from the bottom sheet 12 and the mattress means 11 of the bed 10 by the waterproof layer 13.

The magnitude of the smaller dimensional arrangement of the pad 17 of cover 14 transverse the bed 10 when compared to the waterproof layer 13 will now be described. In particular, in making the bed 10 the waterproof layer 13 is disposed so that the opposite edges thereof which define or coincide with the base of its tails 20 extend approximately midway along the vertical thickness of the mattress means 11 on each side of the mattress means and as shown at 24. Upon placing the cover 14 in position the pad 17 thereof has the opposite edges at the base of its tails disposed in approximately vertically spaced relation above the corresponding opposite side edges at the base of the waterproof layer 13 and as shown at 25, for example. This arrangement assures that the pad 17 will not contact the mattress means 11 and the bottom sheet 12 at opposite ends of the bed 10.

It will also be noted that the dimensions of the pad 17 are such that upon placing the cover 14 in position the pad 17 of such cover has opposite edges thereof at the base of its tails disposed substantially coplanar with the top surface of the bottom sheet 12.

The polymeric layer 13 may be of any suitable thickness and is preferably generally of the order of 6 mils thick, i.e., 0.006 inch thick. Further, the thickness of the pad 17 will depend on the type of threads used to make same and so as to have the approximate weight per square yard mentioned earlier.

It will also be appreciated that the waterproof layer 13 with its tails 15 as well as the cover 14 comprised of pad 17 and its tails 20 in each instance may be suitably laundered using standard or conventional laundering techniques employed at hospitals, nursing homes, or other similar health care facilities. The construction of layer 13 and of cover 14 in each instance is such that each may be laundered a maximum number of times without deterioration while providing optimum cleanliness and sterilization. For example, each item 13 or 14 may be laundered as described at least 50 processes and as high as 100 processes without deterioration thereof due to laundering.

As illustrated in FIG. 3, the cover 14 is basically of rectangular outline. Similarly, the waterproof layer 13 is also of rectangular outline, as shown in FIG. 4. The layer 13 and cover 14 are dimensioned such as to provide optimum protection for the mattress means 11 and bottom sheet 12 of bed 10; and, the tails thereof are dimensioned to hold their respective component firmly in position.

It will be appreciated that the waterproof layer 13 and the pad 17 of cover 14 assure optimum comfort for a patient suffering from incontinence and lying on the pad 17 by absorbing water and moving same away from the patient yet only requiring laundering of the layer and pad upon soiling thereof while protecting the mattress means 10 and bottom sheet 12 against soiling and thereby keeping laundering costs for the hospital, nursing home, or similar health care institution at a minimum.

Terms such as sides, ends, top, and the like have been used in this disclosure to describe certain items as they are illustrated in the drawings. However, it is to be understood that these terms have been used for ease of description and presentation and should not be considered limiting in any way.

While present exemplary embodiments of this invention, and methods of practicing the same, have been illustrated and described, it will be recognized that this invention may be otherwise variously embodied and practiced within the scope of the following claims.

What is claimed is:

1. In a bed for a hospital or the like comprising mattress means, a bottom sheet means covering said mattress means, a waterproof layer covering the central portion of said bottom sheet means, and a cover over said layer, the improvement in which said layer comprises a sheet of moisture impervious polymeric material having opposite ends of a particular width and having top and bottom moisture impervious surfaces in which at least one of said top and bottom surfaces of said sheet is completely exposed, said sheet having a first pair of tails each made of a material which is different than said polymeric material and each having a width equal to said particular width, said first pair of tails extending from and being attached respectively to said opposite ends with each of said first pair of tails being attached along its full width, said cover is made only of three pieces consisting of a water-absorbent pad made of a particular material and having opposite end portions of a given width and having completely exposed top and bottom surfaces of said particular material between said end portions, said pad having a second pair of tails each made of a material which is different than said particular material of said pad and each having a width equal to said given width, said second pair of tails extending from and being attached in an exposed manner respectively against said opposite end portions, each of said second pair of tails being attached along its full width and said first and second pair of tails being adapted to be disposed under said mattress means and defining the sole means holding said layer and pad securely on said bottom sheet means; said layer and pad being separate and readily individually removable from said bed for laundering thereof by pulling the respective tails thereof from under said mattress means.

2. A bed as set forth in claim 1 in which said sheet is a sheet of neoprene rubber.

3. A bed as set forth in claim 2 in which said tails are made of a fabric material.

4. A bed as set forth in claim 1 in which said layer further comprises a scrim material and said sheet is a sheet of neoprene rubber bonded against said scrim material.

5. A bed as set forth in claim 4 in which said scrim material is made of nylon.

6. A bed as set forth in claim 5 in which said pad is comprised of warps and wefts and has a weight of approximately 18 oz. per square yard, and the threads defining either the warps or the wefts consist of roughly 50% cotton threads and 50% polyester threads.

7. A bed as set forth in claim 1 in which said particular material is a woven material of a single thickness weave and is comprised of warps and wefts and the threads defining either the warps or the wefts consist of natural threads and synthetic threads.

8. A bed as set forth in claim 7 in which said natural and synthetic threads consist of 50% cotton and 50% polyester threads.

9. A bed as set forth in claim 8 in which said cotton and polyester threads defining said pad have a weight of approximately 18 oz. per square yard.

10. A bed as set forth in claim 9 in which said tails on said pad are made of a fabric material.

11. In a method of making a bed for a hospital or the like comprising the steps of, providing mattress means, disposing a bottom sheet means in covering relation on said mattress means, placing a waterproof layer over the central portion of said bottom sheet means, and placing a cover over said layer, the improvement in said method in which, said step of placing said layer comprises placing said layer comprised of a sheet of moisture impervious polymeric material having opposite ends of a particular width and having top and bottom moisture impervious surfaces in which at least one of said top and bottom surfaces of said sheet is completely exposed said sheet having a first pair of tails each made of a material which is different than said polymeric material and each having a width equal to said particular width, said first pair of tails extending from said opposite ends with each of said first pair of tails being attached along its full width, said step of placing said cover comprises placing said cover which is made only of three pieces consisting of a water-absorbent pad made of a particular material and having opposite end portions of a given width and having completely exposed top and bottom surfaces of said particular material between said end portions, said pad having a second pair of tails each made of a material which is different than said particular material of said pad and each having a width equal to said given width, said second pair of tails extending from and being attached in an exposed manner respectively against said opposite end portions, each of said second pair of tails being attached along its full width, and disposing said first and second pair of tails under said mattress means as the sole means holding said layer and pad securely on said bottom sheet means, said layer and pad being separate and readily individually removable from said bed for laundering thereof by pulling the respective tails thereof from under said mattress means.

12. A method as set forth in claim 11 in which said step of placing said layer comprises placing said opposite ends of said sheet of said layer so that said opposite ends are disposed approximately midway along the thickness of said mattress means, and said step of placing said cover comprises placing said opposite end portions of said pad of said cover respectively in vertically spaced relation above said opposite ends to assure said pad will not be in contact with said bottom sheet means and thereby prevent any moisture in said pad from being transferred to said bottom sheet means and mattress means.

13. A method as set forth in claim 12 in which said step of placing said cover comprises placing said opposite end portions of said pad of said cover substantially coplanar with said bottom sheet means.

14. A method as set forth in claim 12 in which said steps of placing said layer and placing said cover comprise the preparation steps of attaching said tails to said layer and attaching said tails to said pad of said cover by sewing each tail in position.

15. In a waterproof layer for covering the central portion of a bottom sheet means placed on mattress means of a hospital bed or the like, the improvement wherein said layer is made of a sheet of moisture impervious polymeric material having opposite end portions of a particular width and having completely exposed polymeric top and bottom moisture impervious surfaces between said end portions, and a pair of tails each made of a material which is different than said polymeric material and each having a width equal to said particular width, said pair of tails extending from and being attached respectively to said opposite end portions, each of said tails being attached along its full width and said tails being adapted to be disposed under said mattress means to hold said layer securely on said bottom sheet means of said mattress means.

16. A layer as set forth in claim 15 in which said sheet is a sheet of neoprene rubber.

17. A layer as set forth in claim 16 in which said tails are made of a fabric material.

18. In a cover adapted for use over a waterproof layer which covers the central portion of a bottom sheet means placed on mattress means of a hospital bed or the like, the improvement wherein said cover is made only of three pieces consisting of a water-absorbent pad made of a particular material and having opposite end portions of a given width and having completely exposed top and bottom surfaces of said particular material between said end portions, and a pair of tails each made of a material which is different than said particular material and each having a width equal to said given width, said pair of tails extending from and being attached in an exposed manner respectively against said opposite end portions, each of said tails being attached along its full width and said tails being adapted to be disposed under said mattress means to hold said pad securely on said bottom sheet means, said pad being readily removable from said bed for laundering thereof by pulling said tails from under said mattress means.

19. A cover as set forth in claim 18 in which said particular material is a woven material of a single thickness weave and is comprised of warps and wefts and the threads defining either the warps or the wefts consist of natural threads and synthetic threads.

20. A cover as set forth in claim 19 in which said natural threads are cotton threads, said synthetic threads are polyester threads, and said pad has a weight of approximately 18 ounces per square yard.

* * * * *